(12) United States Patent
Urmey

(10) Patent No.: US 7,699,809 B2
(45) Date of Patent: Apr. 20, 2010

(54) CATHETER POSITIONING SYSTEM

(76) Inventor: William F. Urmey, 1 Flint Ave., Larchmont, NY (US) 10538

( * ) Notice: Subject to any disclaimer, the term of this patent is extended or adjusted under 35 U.S.C. 154(b) by 65 days.

(21) Appl. No.: 11/956,897

(22) Filed: Dec. 14, 2007

(65) Prior Publication Data

US 2008/0147011 A1 Jun. 19, 2008

Related U.S. Application Data

(60) Provisional application No. 60/870,026, filed on Dec. 14, 2006, provisional application No. 60/949,316, filed on Jul. 12, 2007.

(51) Int. Cl.
*A61M 5/178* (2006.01)
*A61N 1/00* (2006.01)
(52) U.S. Cl. .................... 604/165.02; 607/116
(58) Field of Classification Search ............ 604/165.02
See application file for complete search history.

(56) References Cited

U.S. PATENT DOCUMENTS

| 4,615,472 | A | 10/1986 | Nash |
| 4,726,369 | A | 2/1988 | Mar |
| 4,957,117 | A | 9/1990 | Wysham |
| 5,325,746 | A | 7/1994 | Anderson |
| 5,325,868 | A | 7/1994 | Kimmelstiel |
| 5,392,778 | A | 2/1995 | Horzewski |
| 5,423,331 | A | 6/1995 | Wysham |
| 5,505,714 | A * | 4/1996 | Dassa et al. ............ 604/534 |
| 5,630,802 | A | 5/1997 | Moellmann |
| 5,634,475 | A | 6/1997 | Wolvek |
| 5,695,470 | A | 12/1997 | Roussigne |
| 5,871,470 | A * | 2/1999 | McWha ............ 604/158 |
| 6,030,349 | A | 2/2000 | Wilson |
| 6,613,014 | B1 | 9/2003 | Chi |
| 6,949,104 | B2 | 9/2005 | Griffis |
| 2004/0059247 | A1* | 3/2004 | Urmey ............ 600/554 |
| 2006/0217655 | A1* | 9/2006 | Vitullo et al. ............ 604/21 |
| 2006/0267063 | A1 | 11/2006 | McDaniel |

* cited by examiner

*Primary Examiner*—Nicholas D Lucchesi
*Assistant Examiner*—Jason Flick
(74) *Attorney, Agent, or Firm*—Seth Natter; Natter & Natter

(57) ABSTRACT

A system for positioning a catheter includes a nerve stimulator needle carried within the lumen of the catheter. A microelectrode is configured as a needle tip precisely protruding beyond a tapered distal end of the catheter. The catheter and needle are fixed against axial movement relative to one another to maintain the precise configuration of the microelectrode needle tip conductive surface by a releasable clamp which is grasped by the practitioner to compress the catheter lumen against the needle without permanent deformation of the needle shaft while simultaneously advancing the needle and the catheter toward a target nerve.

20 Claims, 4 Drawing Sheets

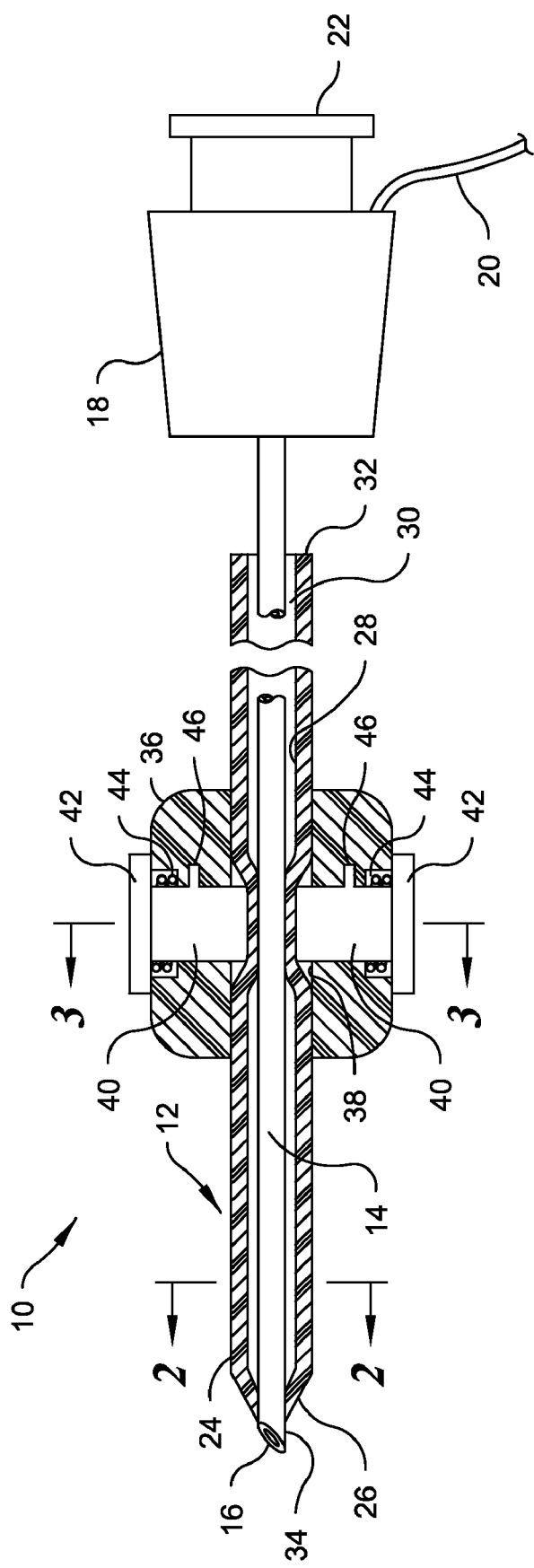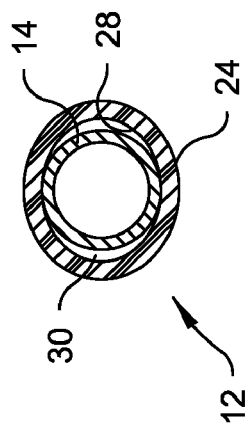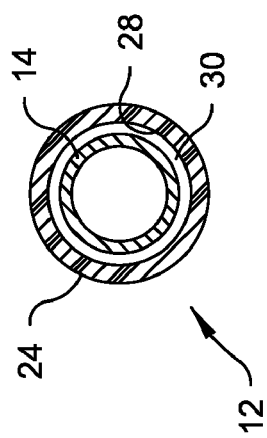

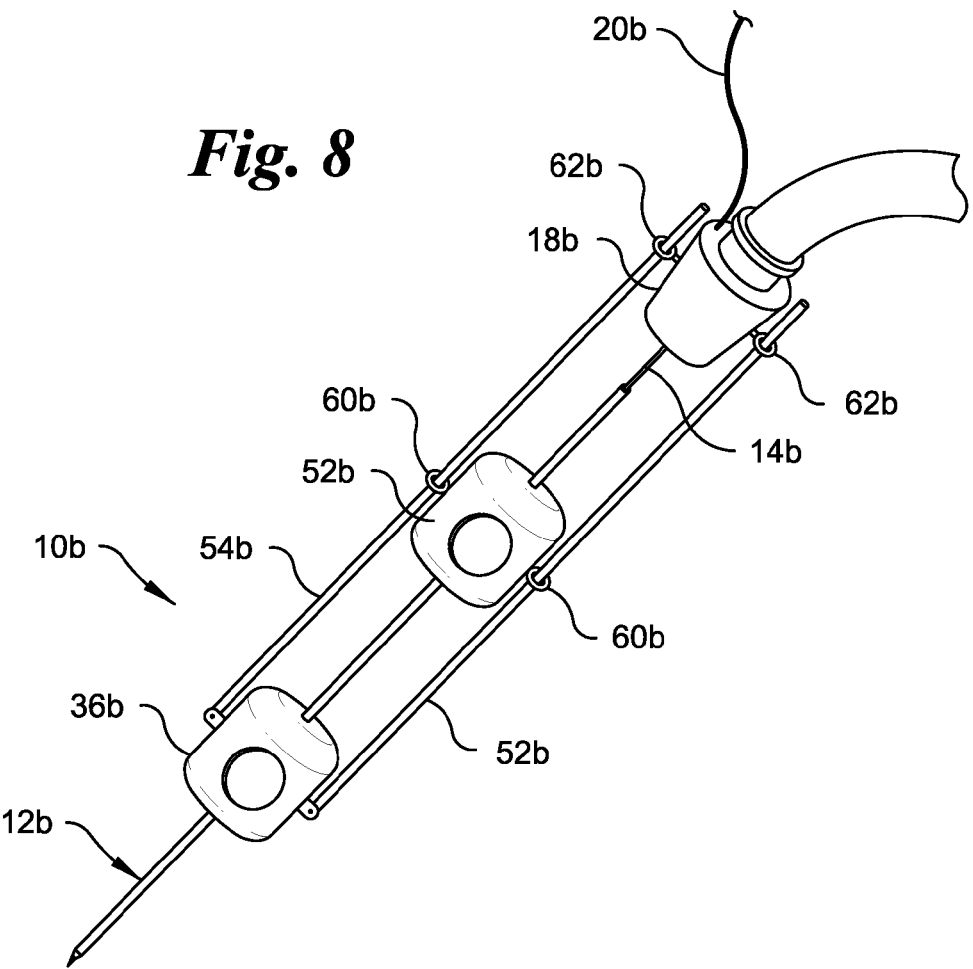
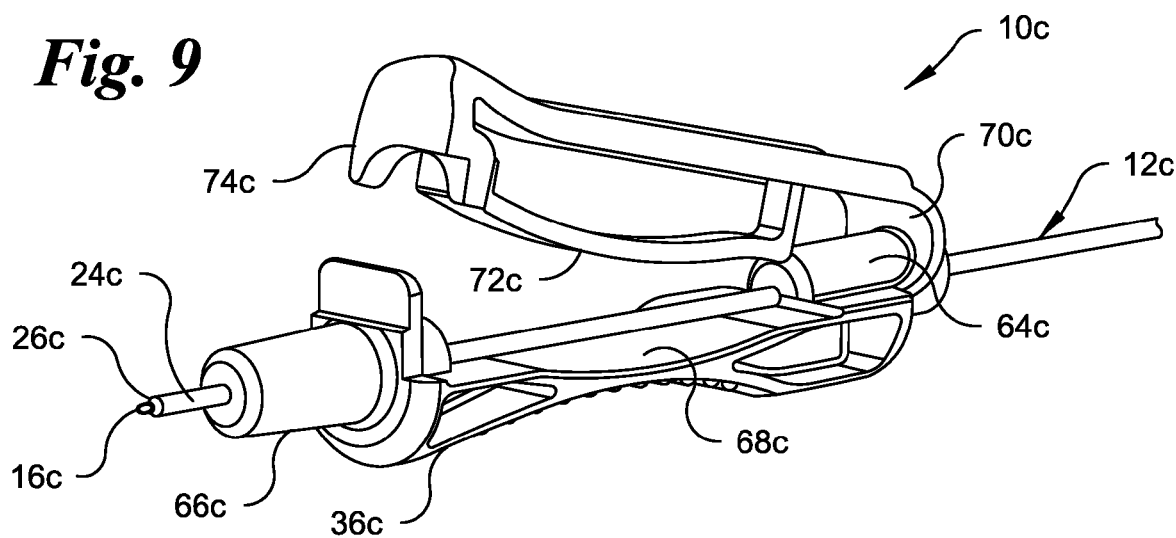

CATHETER POSITIONING SYSTEM

RELATED APPLICATIONS

This application claims the benefit of U.S. Provisional Application No. 60/870,026 filed Dec. 14, 2006 and U.S. Provisional Application No. 60/949,316 filed Jul. 12, 2007, the entireties of both of which are incorporated herein by reference.

BACKGROUND OF THE INVENTION

1. Field of the Invention

This invention relates generally to regional anesthesia and more particularly to a system for positioning a catheter and nerve stimulator needle in conjunction with various procedures, such as, the administration of an anesthetic blockade and for continuous infusion of anesthetic or analgesic through the catheter.

2. Antecedents of the Invention

The field of regional anesthesia relates to the practice of administering anesthesia to a specific body region during surgery, for the relief of postoperative pain, and for extended relief of trauma or chronic pain. Often, regional anesthesia has been found to be preferable to general anesthesia because of increased safety, the availability of postoperative pain control and decreased anesthetic costs.

Regional anesthesia delivery techniques strove to optimize administration of a local anesthetic in close proximity to a target or nerve plexus so as to establish a neural blockade. Successful administration of regional anesthesia was dependent upon the accurate placement of the anesthetic in relation to the target nerve or nerves.

Various techniques have been employed to assist in placement of an administration needle in close proximity to the target nerve, which was not externally visible. One of the traditional methods of needle placement involved eliciting paresthesia. Among the disadvantages of this technique was the lack of accurate patient responses amongst patients who were disoriented and/or sedated.

A prevalent technique employed the use of nerve stimulators electrically coupled to a nerve stimulator needle. Such method was premised upon the phenomenon that an electrical pulse is capable of stimulating a motor nerve fiber to contract an innervated muscle or cause paraesthesia, in the case of sensory nerve stimulation.

The nerve stimulator needle was placed within the tissue of the patient's body in the vicinity of the nerve to be blocked and then advanced until stimulation of the target nerve was achieved as determined by visually detecting muscle contractions or by eliciting a report that the patient felt the stimulus in response to the current flow through the stimulator needle.

The current supplied by the nerve stimulator was reduced as the nerve stimulator needle was further advanced, until stimulation of the target nerve was achieved using a reduced current level associated with a prescribed distance between the needle tip and the target nerve.

Thereafter, a portion of the anesthetic dose was administered through the needle to terminate the response to the nerve stimulation current. If the response was terminated by the initial administration, the needle was deemed to be properly positioned in proximity to the target nerve and the remaining dose of anesthetic was administered and the needle was withdrawn upon completion of the surgical procedure.

Placement of catheters for continuous infusion of local anesthetics or other drugs during surgical procedures and primarily postoperatively has been achieved by use of an intra-catheter which was placed or threaded through the internal lumen of a larger needle or stiff cannula, or by use of an extra-catheter which was placed or threaded over an internal needle or smaller stiff cannula. Each technique has been associated with certain disadvantages and limitations that have resulted in less than optimal results for achieving successful continuous plexus or nerve block in clinical practice. These disadvantages have severely limited the use of continuous anesthesia or analgesia, resulting in under-utilization of continuous techniques in favor of more predictably successful, less invasive and usually less traumatic and therefore safer nerve or plexus blockade utilizing only a nerve stimulation needle for anesthesia or analgesia administration as previously described.

Problems associated with the use of an intra-catheter included the fact that a very large (and therefore more traumatic) introducing needle (e.g. 17 or 18 gauge) was necessary to allow passage of a smaller (usually 19 or 20 gauge) flexible catheter. This caused increase pain and discomfort during the placement. After needle placement, the catheter was passed through the bore of the introducing needle. This technically difficult step could cause movement of the needle tip. Additionally, there was little control of the final position of the distal end of the catheter because the flexibility of the catheter did not allow the practitioner to accurately determine the position of the distal end of the catheter after it passed beyond the needle tip.

Stimulating catheters have been developed with a flexible metal stylet inside the catheter which allowed for the ability to electrically stimulate the nerve or nerves, but these too, were difficult to control in terms of the final positioning of the catheter tip once it passed beyond the needle tip.

Another problem with intra-catheter systems has been persistent leaking of the injected medication at the skin entry point of the removed introducing needle. This occurred because the catheter diameter was smaller than the needle diameter and the diameter of the opening left by the introducing needle. Leakage was especially pronounced after placement of continuous catheters for superficial nerves or nerve plexus.

Major problems associated with the use of an extra-catheter system included the fact that extra-catheters have had to be made of larger gauges than desirable and have been stiffer than desirable to allow adequate stability for advancement over the smaller internal needle. The employment of stiff catheters near nerves for continuous infusion of anesthetics or analgesic medications was undesirable. The stiff catheters could result in nerve trauma.

Smaller, softer and more flexible catheters were preferable for procedures involving continuous infusion. A catheter with the desired flexibility and small diameter was difficult to pass or thread over the needle due to undesired buckling or bending, however. The length of the extra-catheter was therefore limited because longer extra-catheter systems of very small diameter were too flexible and therefore unstable and difficult to pass.

The longer a thin catheter or thin needle was, the more unstable it was. This was because each additional unit of length compounded its flexibility. Such catheters would bend when advanced through the skin and deeper tissues, making targeted accurate placement difficult. Additionally, extra-catheters were required to freely slide off of the internal needle, cannula, or stylet and therefore often had undesired movement in relation to the internal needle during use, especially upon advancement and withdrawal. If the extra-catheter was more tightly fitted to the internal needle, withdrawal of the stylet or needle often put undue traction on the catheter, resulting in undesired movement of the catheter tip from the optimal position that was already achieved.

SUMMARY OF THE INVENTION

A system for positioning a thin, e.g. 22 gauge, catheter includes a thin e.g. 27 gauge, nerve stimulator needle carried within the lumen of the catheter. A microelectrode is configured as a needle tip precisely protruding beyond a tapered distal end of the catheter. The tapered catheter surface reduces trauma upon entry of the needle and catheter and facilitates manipulation of the needle and catheter while searching for the target nerve. The catheter and needle are fixed against axial movement relative to one another to maintain the precise configuration of the microelectrode needle tip conductive surface by a releasable clamp which is grasped by the practitioner to compress the catheter lumen against the needle without permanent deformation of the needle shaft.

The clamp is positioned on the catheter at a relatively short distance, e.g. 2 cm, from the skin entry point to minimize flexure when advancing or withdrawing the catheter needle assembly to simultaneously position the distal end of the catheter and the microelectrode needle tip in close proximity to the target nerve or nerve plexus. The clamp is released upon contacting the skin entry point and is repositioned proximally along the catheter a short distance from the skin entry point. The clamp is then engaged to again compress the catheter against the needle shaft and is employed to further advance the catheter needle assembly as a unit. Optionally, stability may be maintained when accessing deeper nerves utilizing a plurality of clamps positioned sequentially along the length of the catheter, with each clamp being released as it contacts the previously advanced clamp.

Upon attaining the desired needle tip and catheter tip position in proximity to the nerve as determined by electrical stimulation, ultrasonographic imaging, etc., a dosage of anesthetic is administered through the needle. With the clamp or clamps fully or partially released so as to fully open the catheter lumen, the needle can then be freely withdrawn from the catheter while the precisely positioned catheter tip remains in place. The proximal end of the catheter is thereafter coupled to a syringe, tubing, pump or other device for continuous administration of an aesthetic or other medication during a surgical procedure and post operatively.

From the foregoing compendium, it will be appreciated that a feature of the present invention is to provide a catheter positioning system of the general character described which simplifies the continuous administration of neural blockade anesthesia for postoperative pain management.

A consideration of the present invention is to provide a catheter positioning system of the general character described which increases the efficiency of the administration of regional anesthesia.

An aspect of the present invention is to provide a catheter positioning system of the general character described which utilizes a catheter to electrically isolate a nerve stimulator needle shaft except for the tip thereof.

A further consideration of the present invention is to provide a catheter positioning system of the general character described which avoids fluid leakage at the catheter entry point.

To provide a catheter positioning system of the general character described which is well suited for continuous regional anesthesia or analgesia is a further consideration of the present invention.

Yet another aspect of the present invention is to provide a catheter positioning system of the general character described which facilitates simple and accurate positioning of a catheter.

A still further feature of the present invention is to provide a catheter positioning system of the general character described which is relatively low in cost.

An additional consideration of the present invention is to provide a catheter positioning system of the general character described with reduced patient trauma.

A further aspect of the present invention is to provide a catheter positioning system of the general character described with increased efficiency.

Other aspects, features and considerations of the present invention in part will be obvious and in part will be pointed out hereinafter.

With these ends in view, the invention finds embodiment in certain combinations of elements, arrangements of parts and series of steps by which the aforesaid aspects, features and considerations and certain other aspects, features and considerations are attained, all with reference to the accompanying drawings and the scope of which will be more particularly pointed out and indicated in the appended claims.

BRIEF DESCRIPTION OF THE DRAWINGS

In the accompanying drawings in which are shown some of the various exemplary embodiments of the invention, it should be understood that the drawings are for illustrative purposes only and the components illustrated therein may not be drawn to scale relative to one another throughout the various views:

FIG. 1 is an enlarged scale sectional view through a catheter needle assembly of a catheter positioning system embodying the present invention and showing a nerve stimulator needle positioned within the lumen of a catheter and a releasable clamp compressing the catheter against the shaft of the nerve stimulator needle;

FIG. 2 is an enlarged scale sectional view through the catheter needle assembly taken substantially along the line 2-2 of FIG. 1 and showing a clearance space between the lumen of the catheter and the needle shaft;

FIG. 3 is an enlarged scale sectional view taken substantially along the line 3-3 of FIG. 1 with the releasable clamp deleted to better illustrate the compressed state of the catheter wall portions registered with the clamp, such that the catheter wall portions contact and grip the needle shaft, preventing axial movement between the catheter and the needle.

FIG. 8 is a perspective illustration of a further embodiment of the catheter positioning system having an alternate arrangement for linking releasable clamps with stringer rods extending from a first clamp through brackets formed in a successive clamp and through brackets formed in a needle hub; and FIG. 9 is a perspective illustration of a catheter positioning system with a preferred alternate releasable clamp.

DESCRIPTION OF THE PREFERRED EMBODIMENTS

Figure 4:
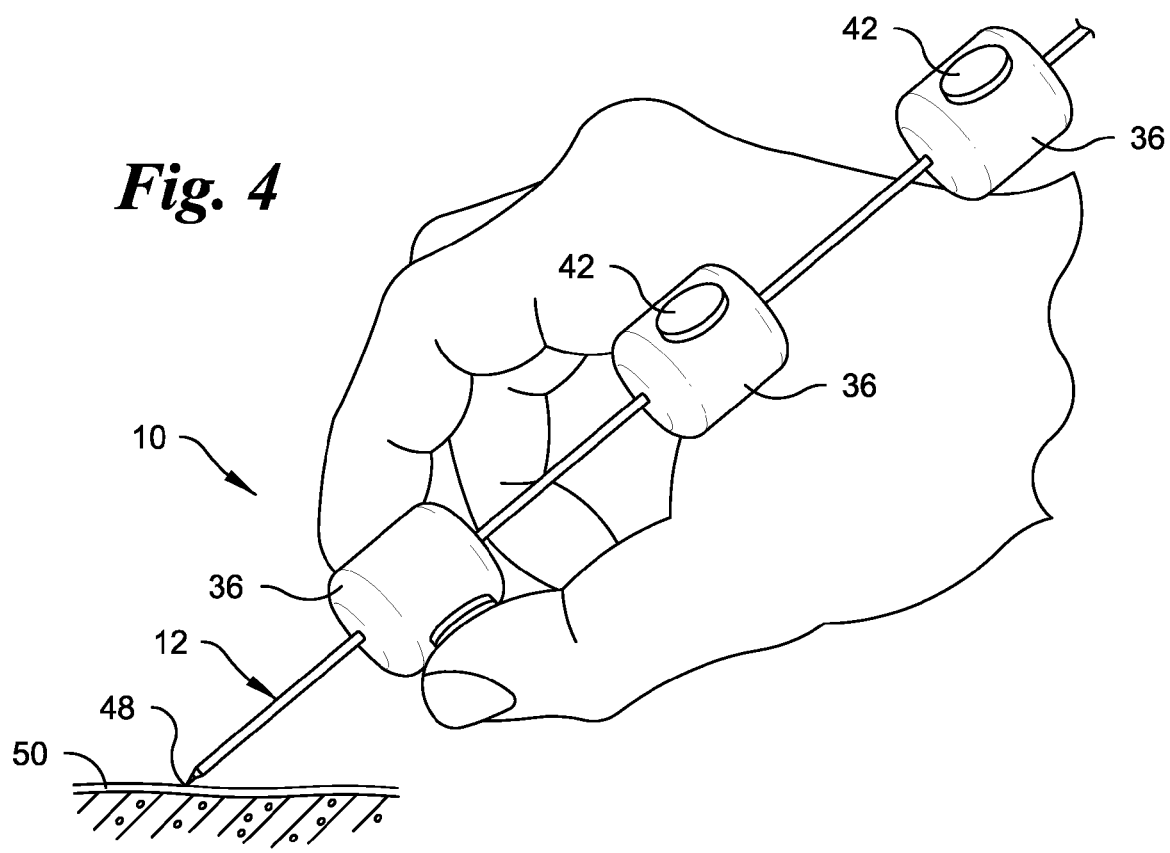
FIG. 4 is a diagrammatic elevational view illustrating a practitioner advancing a catheter needle assembly at an entry point on a patient's skin by grasping and advancing a releasable clamp and actuating the clamp to compress the catheter against the needle shaft, fixing the needle shaft against axial movement relative to the catheter.

Referring now in detail to the drawings, wherein like numerals designate like components throughout, the reference numeral 10 denotes generally a catheter positioning system constructed in accordance with and embodying the invention. The catheter positioning system 10 includes a catheter needle assembly 12 comprising a thin, e.g. 27 gauge, nerve stimulator needle 14 having a sharp cutting tip 16 at a distal end and a conventional hub 18 at a proximal end. The hub 18 includes an electrical lead 20 which is coupled to a conventional nerve stimulator (not shown) and a fitting 22 suitable for receiving tubing from a syringe, for example, for administration of an anesthetic of other medicine through the bore of the nerve stimulator needle 14.

A thin, e.g. 22 gauge, catheter 24 includes a tapered distal end 26 and a lumen 28 which receives the shaft of the nerve stimulator needle 14. The diameter of the lumen 28 is greater than the diameter of the needle shaft, leaving a clearance space 30 such that if unrestrained, the needle 14 may move axially relative to the catheter 24 with relative freedom. A proximal end 32 of the catheter 24 is spaced from the needle hub 18.

Pursuant to the invention, the needle tip 16 and a surface 34 of the needle shaft which projects beyond the tapered distal end 26 of the catheter comprises a precisely dimensioned and defined microelectrode for nerve stimulation. As such, the shaft of the nerve stimulator needle 14 need not have an electrically insulated coating. For effective catheter needle assembly guidance, the dimensional geometry of the projecting portion of the needle must remain constant (fixed) while steering the nerve stimulator needle tip and catheter distal end 26 toward or away from a target nerve or nerve plexus during the search for the target nerve or nerve plexus.

Pursuant to the invention, there is provided one or more releasable clamps 36 through which the catheter needle assembly 14 extend. Illustrated in FIG. 1 is an exemplary releasable clamp 36 having a bore 38 through which the catheter needle assembly is threaded and a pair of diametrically opposed cylindrical gates 40 which extend along an axis perpendicular to the axis of the bore 38. Each gate includes an enlarged head 42. Positioned within annular channels registered with the heads 42 are a pair of coil springs 44 which urge the gates 40 radially outwardly to a released position, wherein the clearance space 30 is maintained. By pressing both heads 42 inwardly, the gates deform the conduit 24 to axially fix the conduit 24 relative to the needle shaft, as illustrated in FIG. 3.

The compressed state of the gates can be locked by rotating the heads 42, such that a radially projecting pin 46, normally seated in an axial groove, extends into an annular notch or groove. The gates are released by rotating the heads 42 in the opposite direction to reseat the pins in their axial grooves.

A clamp 36 having a single gate 40 may also be employed, with the catheter being compressed between the single gate and the diametrically opposed portion of the bore 38 to fix the conduit relative to the needle shaft.

It should be understood that the releasable clamp 36 as illustrated in FIG. 1 is merely shown in an exemplary manner; any suitable releasable clamp may be employed, such as those described in U.S. Pat. Nos. 6,949,104; 5,634,475; 5,423,331; 5,392,778; 5,325,476; 4,957,117; 4,726,369 and 4,615,472 and U.S. Patent Application Publication No. 2004/0059247, all of which are incorporated herein by reference. Further, a compression unit available from B. Braun Melsungen AG of Melsungen, Germany designated as catheter connectors for use with 19 gauge spring wound catheters, Product Code #PCC 100 FX, Reference No. 332241.

Referring now to FIG. 4, the catheter needle assembly is shown in an operative position prior to penetration of the nerve stimulator needle tip 16 through an entry point 48 prelocated on a patient's skin 50. It should be noted that a releasable clamp 36, which is positioned approximately 2 cm from the needle tip 16, is grasped between the thumb and forefinger of a practitioner. The practitioner engages the releasable clamp 36 against the catheter 24 and needle 14, such that the catheter 24 is deformed, as illustrated in FIG. 3 to axially fix the catheter and needle. Such deformation is maintained as the clamp 36 is advanced toward the entry point 48 with the tip 16, piercing the patient's dermal layers to introduce the catheter needle assembly through dermal layers and subcutaneous tissue while seeking a target nerve. It should be understood that the catheter 24, which is axially fixed to the needle 14 by the clamp 36, moves with the needle as a unit and that the clamp 36 is manipulated, not only in an axial direction, but pivotally about the entry point 48 while approaching a target nerve.

Figure 5:
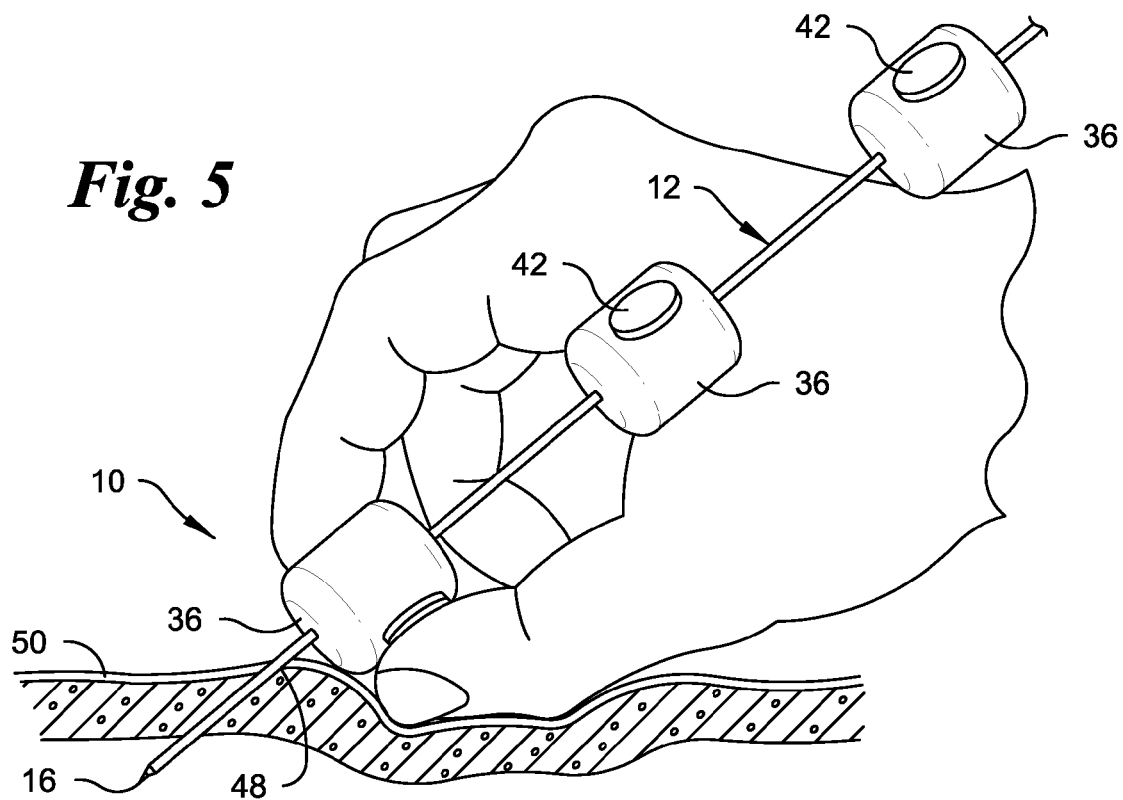
FIG. 5 is an illustration, similar to that of FIG. 4, showing the position of the catheter and releasable clamp after the catheter and needle have been advanced through the skin and subcutaneous tissue to a point where the clamp contacts the skin and cannot be advanced further.

FIG. 5, similar to FIG. 4, illustrates the relative position of the grasped clamp 36 and the catheter needle assembly 12 at a point where the grasped clamp 36 can no longer be advanced.

At this point, if the catheter needle assembly includes multiple spaced releasable clamps 36, the practitioner releases the clamp 36 which is abutting the skin 50. The next sequential clamp 36 is then grasped and engaged or has been previously locked to fix the needle shaft to the catheter by deforming the catheter. The practitioner may then employ the nondominant hand to stabilize the released clamp positioned at the entry point 48, while the practitioner's dominant hand continues to advance the catheter needle assembly into the patient in search of the target nerve or nerve plexus.

Figure 6:
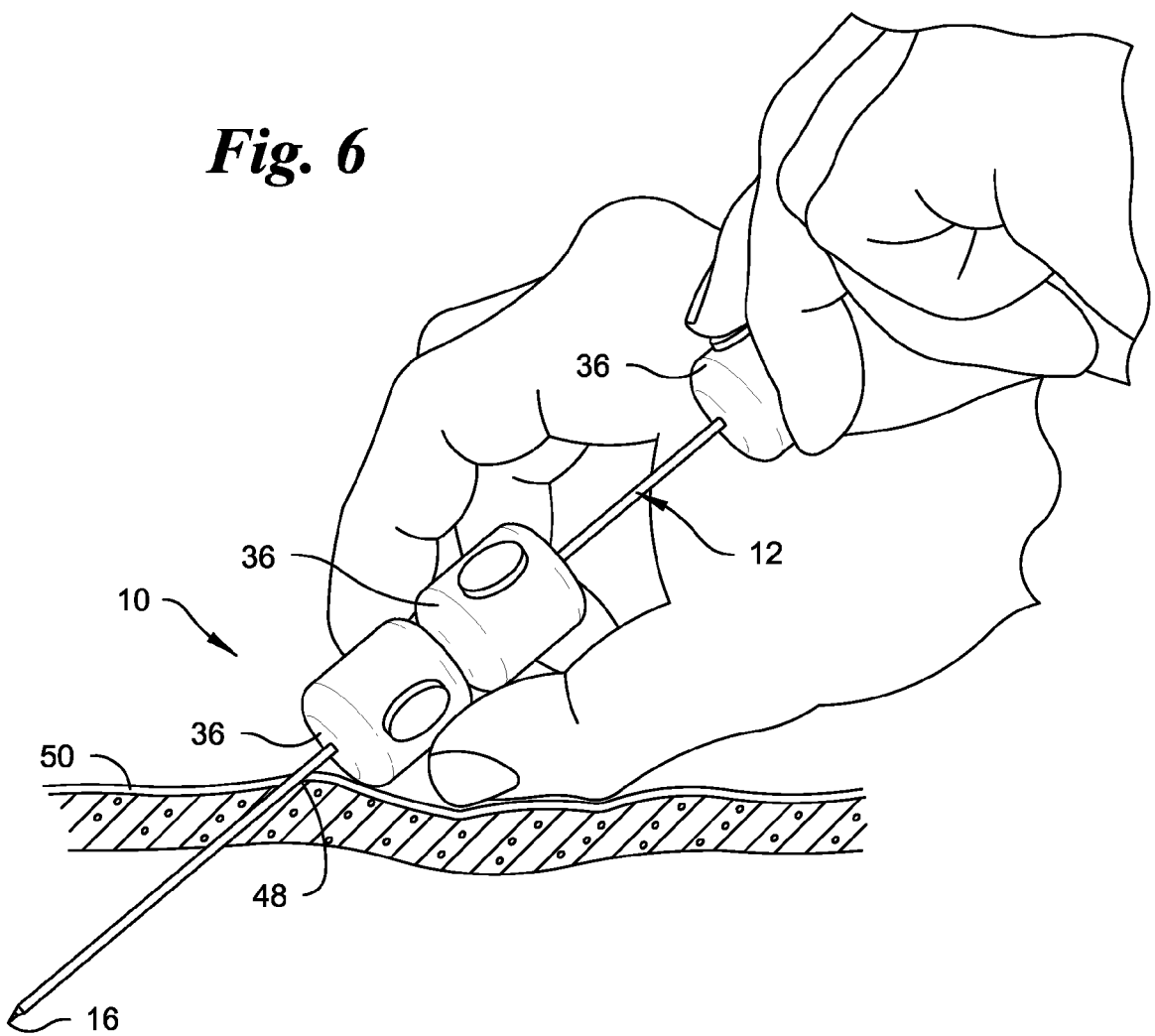
FIG. 6 is an illustration, similar to FIGS. 4 and 5, depicting the position of the catheter needle assembly after the catheter needle assembly has been extended into the patient an additional distance, utilizing a second releasable clamp.

FIG. 6 illustrates this continued procedure wherein a pair of released clamps are stabilized adjacent the entry point 48 by the practitioner's nondominant hand during further advancement and manipulation of the catheter needle assembly in search of the target nerve or nerve plexus.

It should be appreciated that because the engaged clamp 36 is positioned only a short distance from either the entry point 48 or the stabilized previously positioned and released clamps 36, flexure of the catheter needle assembly between the engaged clamp and the entry point 48 is greatly reduced and precise control and guidance of the catheter needle assembly is achieved.

Figure 7:
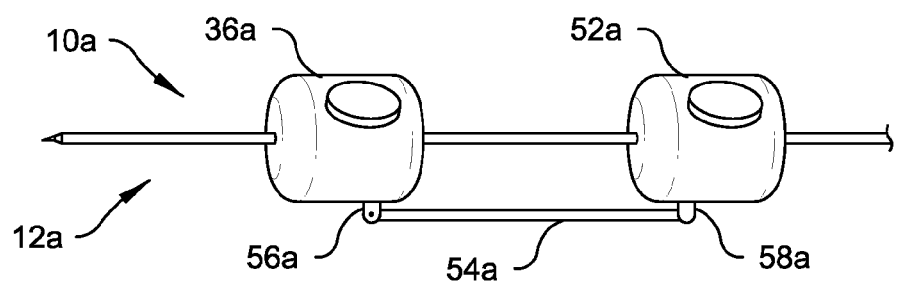
FIG. 7 is fragmentary elevational view of an alternate catheter positioning system having a pair of linked releasable clamps for increasing the stiffness of the catheter needle assembly.

In FIG. 7, a fragmentary view of an alternate embodiment of the catheter positioning system of the present invention is illustrated. Like numerals will be employed to denote like components of the previous embodiment, however bearing the suffix "a".

A catheter positioning system 10*a* includes a catheter needle assembly 12*a* substantially identical to that described with respect to the previous embodiment. The catheter positioning system 10*a*, differs, however from that of the previous embodiment through the linking of successive releasable clamps positioned along the catheter needle assembly 12*a*.

The portion of the catheter needle assembly positioned between a releasable clamp being gripped and manipulated by the practitioner and the next sequential clamp is rigidified to facilitate manipulation of the portion extending distally, i.e. between the releasable clamp being gripped and the needle tip 16a.

More specifically, the catheter positioning system 10a includes a plurality of releasable clamps, with two clamps 36a, 52a being illustrated by way of example only. The distally positioned clamp 36a is linked to the proximally positioned clamp 52a by a rigid stringer rod 54a. The stringer rod 54a is pivotally joined to the releasable clamp 36a at a hinge bracket 56a and is releasably joined to the clamp 52a at a bracket 58a. The axial catheter needle assembly span between the brackets 36a, 52a is thus supported against deflection by the stringer rod 54a.

It should be noted that after the clamp 36a contacts the patient's skin adjacent the entry point, the stringer rod 54a is released from the bracket 58a so that the practitioner may advance the catheter needle assembly further by grasping and manipulating the clamp 52a.

Referring now to FIG. 8 wherein a further embodiment of the invention, similar to the embodiment of FIG. 7 is illustrated, it should be noted that like numerals will be employed to denote like components of the prior embodiments, however bearing the suffix "b".

A catheter positioning system 10b includes a catheter needle assembly 12b substantially identical to those described with reference to the previous embodiments and having an initial releasable clamp 36b and a further releasable clamp 52b. It should be understood, however, that in practice, the releasable clamp 52b will not necessarily be required and the clamp 36b may be sequentially repositioned along the catheter needle assembly.

In the present embodiment, a pair of diametrically opposed stringer rods 54b extend proximally from the releasable clamp 36b and are slidably received through a pair of eyelets 62b which project radially from a hub 18b of a stimulator needle 14b. The stringer rods 52b may also pass through eyelets 60b which project from the further releasable clamp 52b. The stringer rods 54b serve to stiffen the entire portion of the catheter needle assembly 12b, which extends proximally from the clamp 36b.

Referring now to FIG. 9 wherein a further preferred embodiment of releasable clamp is illustrated, like numerals will again be employed to denote like components of the previous embodiments however bearing the suffix "c".

A releasable clamp 36c is formed of one piece molded thermoplastic construction and includes a pair of axially registered generally cylindrical proximal and distal guideways 64c, 66c through which a catheter needle assembly 12c extends. It should be noted that the portion of the catheter needle assembly projecting from the distal guideway 66c includes a nerve stimulator needle tip 16c and a distal end taper 26c of a catheter 24c.

The releasable clamp 36c includes a concave platen 68c which extends between the guideways 64c, 66c. A flexible leaf hinge 70c joins the proximal guideway 64c to a maxillary convex jaw 72c. A yoke 74c, at the distal end of the convex jaw 72c which contacts the guideway 66c to limit the travel of the convex jaw 72c and prevent permanent deformation of the nerve stimulator needle. In use, a practitioner grasps the outer surfaces of the convex jaw and the concave platen between the forefinger and thumb and squeezes the jaw and platen together.

It should be appreciated that when the convex jaw 72c is urged against the concave platen 68c, the convex jaw contacts the catheter and deforms it toward the concave platen 68c such that the catheter and the needle are fixed against axial movement relative to one another. The arc of curvature of the mating convex jaw and concave platen may be such to slightly bend, but not permanently deform the nerve stimulator needle.

Thus is will be seen that there is provided a catheter positioning system of the general character described which achieves the various aspects, features and considerations of the present invention and is well suited to meet the conditions of practical usage.

As various possible further embodiments might be made of the present invention and various changes might be made in the illustrative embodiments above set forth without departing from the spirit of the invention, it is to be understood that all matter herein described or shown in the accompanying drawings is to be interpreted as illustrative and not in a limited sense.

Having thus described the invention, there is claimed as new and desired to be secured by Letters Patent:

1. A system for positioning a flexible catheter proximate a target nerve or nerve plexus of a subject, the system comprising a catheter needle assembly, the assembly including a catheter having a distal end, a proximal end and a lumen, a nerve stimulator needle, the needle including a shaft positioned within the lumen, the shaft having a diameter less than that of the lumen leaving a clearance space, the needle having a sharp tip, the sharp tip projecting beyond the distal end of the catheter, the system further including a releasable clamp positioned over the catheter, the clamp being in an engaged configuration wherein the clamp is fixed relative to the catheter and compresses the catheter lumen against the needle shaft to fix the catheter and needle shaft against axial displacement relative to one another and to maintain the position of the sharp tip relative to the distal end of the catheter, the engaged configuration clamp being manipulated to advance the sharp tip and distal end of the catheter toward a target nerve or nerve plexus, the clamp being repositionable along the length of the catheter when in a disengaged configuration.

2. A system for positioning a flexible catheter as constructed in accordance with claim 1 wherein the releasable clamp is positioned along the catheter a distance of approximately 2 cm from the distal end of the catheter, the clamp stiffening the portion of the catheter needle assembly between the distal end of the catheter and the clamp, whereby introduction of the catheter needle assembly through dermal layers of the subject and the advancement of the needle tip toward the target nerve or nerve plexus is facilitated.

3. A system for positioning a flexible catheter as constructed in accordance with claim 1 wherein the distal end of the catheter is tapered, whereby trauma upon introduction of the catheter needle assembly through dermal layers and subcutaneous tissue and during manipulation toward the target nerve or nerve plexus is minimized.

4. A system for positioning a flexible catheter as constructed in accordance with claim 1 wherein the needle shaft has a length greater than the length of the catheter.

5. A system for positioning a flexible catheter as constructed in accordance with claim 1 further including a hub affixed to the proximal end of the needle, the hub including an electrical lead for coupling the needle tip to a nerve stimulator.

6. A system for positioning a flexible catheter as constructed in accordance with claim 5 further including at least one stringer rod extending from the releasable clamp toward the hub, the stringer rod engaging the hub, whereby the portion of the catheter needle assembly between the releasable clamp and the hub is supported against deflection.

7. A system for positioning a flexible catheter as constructed in accordance with claim 1 wherein a plurality of releasable clamps are provided, each releasable clamp being positioned over the catheter and the needle shaft.

8. A system for positioning a flexible catheter as constructed in accordance with claim 7 further including at least one stringer rod extending between two releasable clamps, the stringer rod serving to rigidify the portion of the catheter needle assembly between the linked releasable clamps.

9. A system for positioning a flexible catheter as constructed in accordance with claim 1 wherein the portion of the needle projecting beyond the distal end of the catheter comprises a microelectrode.

10. A method of positioning a flexible catheter having a lumen proximate a target nerve or nerve plexus, the method comprising the steps of:
  a) providing a nerve stimulator needle having a diameter less than that of the catheter lumen,
  b) positioning the needle shaft within the lumen,
  c) extending the needle tip beyond the distal end of the catheter,
  d) positioning a releasable clamp on the catheter,
  e) engaging the clamp to preclude movement of the clamp relative to the catheter and compress the catheter against the needle shaft to preclude movement of the needle tip relative to the distal end of the catheter,
  f) advancing the catheter and needle through dermal layers and toward the target nerve or nerve plexus by grasping and manipulating the engaged clamp,
  g) disengaging the clamp to permit relative axial movement of the needle shaft relative to the catheter when the catheter is positioned proximate the target nerve or nerve plexus and
  h) withdrawing the needle shaft while maintaining the catheter in position.

11. A method of positioning a flexible catheter in accordance with claim 10 further including the step of:
  i) disengaging and repositioning the releasable clamp along the catheter if the releasable clamp can no longer be advanced prior to performing step g).

12. A method of positioning a flexible catheter in accordance with claim 10 wherein step d) includes positioning a plurality of releasable clamps on the catheter and steps e) and f) are performed in connection with the releasable clamp positioned closest to the distal end of the catheter, the method further including the step of disengaging the releasable clamp if the releasable clamp can no longer be advanced prior to performing step g) and thereafter performing steps e), f), g) and h) with a further releasable clamp.

13. A system for positioning a flexible catheter proximate a target nerve or nerve plexus of a subject, the system comprising a catheter needle assembly, the assembly including a catheter having a distal end, a proximal end and a lumen, a nerve stimulator needle, the needle including a shaft positioned within the lumen, the shaft having a diameter less than that of the lumen leaving a clearance space, the needle having a sharp tip, the sharp tip projecting beyond the distal end of the catheter, a distal portion of the needle projecting beyond the distal end of the catheter, the system further including a releasable clamp positioned over the catheter and the needle shaft, the clamp having an engaged position, wherein the clamp is fixed relative to the catheter and compresses the catheter lumen against the needle shaft to fix the catheter and needle shaft against axial displacement relative to one another and maintain the position of the projecting distal portion of the needle relative to the distal end of the catheter, the engaged position clamp being manipulated to advance the sharp tip and distal end of the catheter toward a target nerve or nerve plexus.

14. A system for positioning a flexible catheter as constructed in accordance with claim 13 wherein the releasable clamp is positioned along the catheter a distance of approximately 2 cm from the distal end of the catheter, the clamp stiffening the portion of the catheter needle assembly between the distal end of the catheter and the clamp, whereby introduction of the catheter needle assembly through dermal layers of the subject and advancement toward the target nerve or nerve plexus is facilitated.

15. A system for positioning a flexible catheter as constructed in accordance with claim 13 wherein the distal end of the catheter is tapered, whereby trauma upon introduction of the catheter needle assembly through dermal layers and subcutaneous tissue and during manipulation toward the target nerve or nerve plexus is minimized.

16. A system for positioning a flexible catheter as constructed in accordance with claim 13 wherein a plurality of releasable clamps are provided, each releasable clamp being positioned over the catheter and the needle shaft.

17. A system for positioning a flexible catheter as constructed in accordance with claim 16 further including at least one stringer rod extending between two releasable clamps, the stringer rod serving to rigidify the portion of the catheter needle assembly between the linked releasable clamps.

18. A system for positioning a flexible catheter as constructed in accordance with claim 13 wherein the portion of the needle projecting beyond the distal end of the catheter comprises a microelectrode.

19. A system for positioning a flexible catheter as constructed in accordance with claim 13 further including a hub affixed to the proximal end of the needle, the hub including an electrical lead for coupling the microelectrode to a nerve stimulator.

20. A system for positioning a flexible catheter as constructed in accordance with claim 13 when the releasable clamp includes a bore, the catheter needle assembly extending through the bore.

* * * * *